United States Patent [19]

Witkowski et al.

[11] 3,948,885

[45] Apr. 6, 1976

[54] 5-HYDROXYL-1,2,3-TRIAZOLE-4-CARBOXAMIDE NUCLEOSIDE

[75] Inventors: Joseph T. Witkowski, Laguna Niguel; Roland K. Robins, Santa Ana; Frank A. Lehmkuhl, Costa Mesa, all of Calif.

[73] Assignee: ICN Pharmaceuticals, Inc., Irvine, Calif.

[22] Filed: Mar. 19, 1973

[21] Appl. No.: 342,616

[52] U.S. Cl........ 260/211.5 R; 260/308 A; 424/180
[51] Int. Cl.²........................................ C07H 19/04
[58] Field of Search ............................ 260/211.5 R

[56]  References Cited
UNITED STATES PATENTS 3,470,196  9/1969  Harvey............................ 260/308 A
3,598,807  8/1971  Nakayama et al. ........... 260/211.5 R

OTHER PUBLICATIONS

Alonso, G. et al., "J. Hetero. Chem.," Vol. 7, 1970, pp. 1269–1272.
Witkowski, J. T. et al., "J. Org. Chem.," Vol. 35, No. 8, 1970, pp. 2635–2639.
Tipson, "Advances in Carbohydrate Chemistry and Biochemistry," Vol. 25, Academic Press, New York, N.Y., 1970, pp. 387–388.

Primary Examiner—Johnnie R. Brown
Attorney, Agent, or Firm—Thomas D. Kiley; Kay H. Boswell

[57]  ABSTRACT

A 5-hydroxy-1,2,3-triazole-4-carboxamide nucleoside, related to the C-nucleoside pyrazomycin, is facilely synthesized by condensation of acyl-blocked ribofuranose with trimethylsilylated 5-hydroxy-1,2,3-triazole-4-carboxamide or, alternatively, by cycloaddition of suitably blocked β-D-ribofuranosyl azide and the anion of ethyl malonamate, and demonstrated to exhibit antiviral properties. The triazole precursor of the former route, as well as certain of its novel salts, are also disclosed as potential antiviral agents.

2 Claims, No Drawings

5-HYDROXYL-1,2,3-TRIAZOLE-4-CARBOXAMIDE NUCLEOSIDE

BACKGROUND OF THE INVENTION

Pyrazomycin is a nucleoside of structure

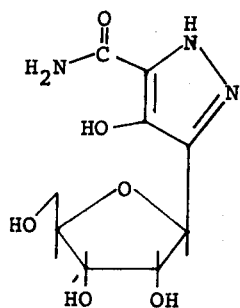

first isolated from a fermentation broth of a strain of Streptomyces candidus characterized in U.S. Pat. No. 3,674,774 as "hitherto unknown". Like the triazole nucleoside 1-β-D-ribofuranosyl-1,2,4-triazole-3-carboxamide [J. T. Witkowski, et al, J. Med. Chem. 15, 1150 (1972) R. W. Sidwell et al, Science, 177, 705 (1972)] pyrazomycin exhibits a substantial range of antiviral activity, which in at least the latter case is apparently related to competition with uridine metabolism. Unlike the former compound, however, pyrazomycin is a C-nucleoside, and a degree of toxicity associated with its employment in vivo (e.g., D. C. Delong, et al, Abstracta, VIIth International Congress of Chemotherapy, Prague, August 1971, A-5/35) may arise from resistance to detoxification occasioned by the stability of the C-glycosidic linkage. Like other C-nucleosides, pyrazomycin resists facile synthesis, although H. Farkas and others, in Tetrahedron Letters, 2279 (1972) have recently reported its obtainment by a protracted procedure commencing with ozonolytical cleavage of another C-glycoside. To our knowledge, no less inconvenient synthetic preparation of pyrazomycin appears in the literature.

BRIEF SUMMARY OF THE INVENTION

According to this invention, the nucleoside 5-hydroxy-1-β-D-ribofuranosyl-1,2,3-triazole-4-carboxamide is facilely prepared and demonstrated to exhibit antiviral activity, providing for the first time an antimetabolite N-nucleosidic analog of the antiviral C-nucleoside pyrazomycin.

DETAILED DESCRIPTION OF THE INVENTION

The synthesis of 5-hydroxy-1-β-D-ribofuranosyl-1,2,3-triazole-4-carboxamide (1) was approached by two routes as follows.

Treatment of the trimethylsilyl derivative of 4-hydroxy-1,2,3-triazole-5-carboxamide [O. Dimroth, Ann., 373, 344 (1910] with 1-O-acetyl-2,3,5-tri-O-benzoyl-β-D-ribofuranose in the presence of stannic chloride provided, after deblocking, a mixture of two isomeric nucleosides. The isomers were separated by chromatography over cellulose and the major product was identified as 5-hydroxy-1-β-D-ribofuranosyl-1,2,3-triazole-4-carboxamide (1) by comparison with a sample prepared by an unambiguous route described below. The structure of the isomeric product (2) is tentatively assigned as 4-hydroxy-2-β-D-ribofuranosyl-1,2,3-triazole-5-carboxamide.

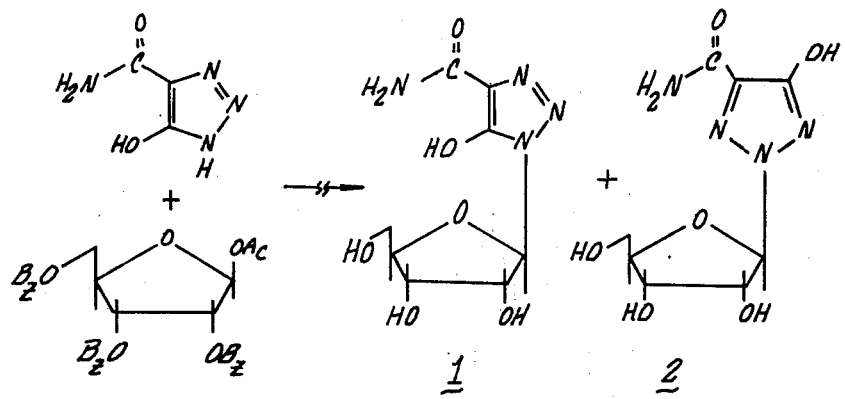

An alternative route to 1 involves cycloaddition of 2,3,5-tri-O-benzoyl-β-D-ribofuranosyl azide [J. Baddiley et al, J. Chem. Soc. 4769 (1957)] with an active methylene compound (see below). A similar route has recently been utilized in the synthesis of 5-amino-1-β-D-ribofuranosyl-1,2,3-triazole-4-carboxamide [Hutzenlaub et al, J. Med. Chem., 15, 879 (1972)].

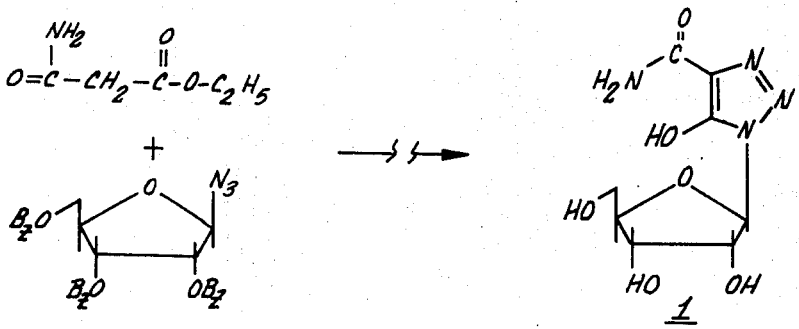

Treatment of the ribosyl azide with the anion of ethyl malonamate provided, after debenzoylation and chromatography, the nucleoside 1. Cycloaddition reactions of enolate anions with azides are known to proceed with the formation of 1-substituted-5-hydroxy-1,2,3-triazoles [M. Begtrup, Acta Chem. Scand., 18, 1333 (1964)], which serves to establish the structure of the nucleoside 1. In addition, the β-configuration of 1 follows from the known configuration of 2,3,5tri-O-benzoyl-β-D-ribofuranosyl azide (J. Baddiley et al, supra).

The 5'-phosphate of compound 1 is also prepared by the cycloaddition route, employing in this case β-D-ribofuranosyl azide 5-O-phosphate (Carrington et al, Journal of the Chemical Society, 1965, 6864). By analogy to the 5'-phosphates of pyrazomycin (F. Streightoff et al, 9th Conf. on Antimicrob. Agents and Chemotherapy, Wash., D.C. 1969, Abstract No. 18) and 1-β-D-ribofuranosyl-1,2,4-triazole-3-carboxamide, this compound may be expected to exhibit in useful degree the antiviral activity of the nucleoside.

As demonstrated in the Examples of preferred preparations which follow, compound 1 has exhibited in vitro activity against measles and Type 1 herpes simplex viruses. We have also discovered similar activity to reside in the precursor base, 4-hydroxy-1,2,3-triazole-5-carboxamide and in its novel sodium salt. Physiologically acceptable water soluble alkaline earth and alkali metal (eg, sodium or potassium) salts may be secured as by the general procedure of Example 2, infra, with appropriate choice of ethoxide reagent, and other such salts (eg, ammonium or alkylamine) there secured by, eg, ion exchange.

The manner in which the compounds of the invention may be used generally follows the disclosures contained in the commonly assigned applications of Richard L. Tolman et al (Ser. No. 265,482 filed June 23, 1972) now U.S. Pat. No. 3,836,645, and J. T. Witkowski et al (Ser. No. 340,332, filed Mar. 12, 1973) respectively for "3-Deazanucleosides" and "1,2,4-Triazole-3-Carboxamides as Antiviral Agents". The disclosures of those applications are incorporated herein by reference.

The invention is further illustrated in the examples which follow.

EXPERIMENTAL 1. 4-Hydroxy-1,2,3-triazole-5-carboxamide (3)

To a solution of sodium ethoxide obtained from sodium (2.3 g, 0.10 mole) and absolute ethanol (150 ml) was added malondiamide (10.2 g, 0.10 mole). The mixture was stirred until most of the malondiamide dissolved. p-Toluenesulfonyl azide (19.7 g, 0.10 mole) was dissolved in ethanol (20 ml) and added dropwise with stirring. The thick mixture was stirred at room temperature for 30 min and heated under reflux in an oil bath for an additional 30 min. The mixture was cooled and the sodium salt was removed by filtration and washed with ethanol followed by ether. The salt was dissolved in a minimum of hot water and the solution was acidified to pH 2 with dilute hydrochloric acid. Upon cooling, the product crystallized. The compound was recrystallized from water to give 9.0 g of the known compound 4-hydroxy-1,2,3-triazole-5-carboxamide, m.p. 191°–192°.

Anal. Calcd. for $C_3H_4N_4O_2$: C, 28.13; H, 3.15; N, 43.75. Found: C, 27.92; H, 3.06; N, 43.60.

2. 4-Hydroxy-1,2,3-triazole-5-carboxamide Sodium Salt Monohydrate (4)

To a solution of sodium ethoxide obtained from sodium (2.3 g, 0.10 mole) and absolute ethanol (150 ml) was added malondiamide (10.2 g, 0.10 mole). The mixture was stirred until most of the malondiamide dissolved. p-Toluenesulfonyl azide (19.7 g, 0.10 mole) was dissolved in ethanol (20 ml) and added dropwise with stirring. The thick mixture was stirred at room temperature for 30 min and heated under reflux in an oil bath for an additional 30 min. The mixture was cooled and the sodium salt was removed by filtration and washed with ethanol followed by ether. The salt was recrystallized from water-ethanol to give 8.3 g of 4-hydroxy-1,2,3-triazole-5-carboxamide sodium salt monohydrate, m.p. 320° (dec.).

Anal. Calc. for $C_3H_3N_4O_2Na.H_2O$: C, 21.43; H, 2.99; N, 33.33. Found: C, 21.35; H, 3.06; N, 33.21.

3. Trimethylsilyl Derivative of 5-Hydroxy-1,2,3-triazole-4-carboxamide

The trimethylsilyl derivative was prepared by the method of Wittenburg, Z. Chem. 4, 303 (1964). A mixture of 5-hydroxy-1,2,3-triazole-4-carboxamide (1.41 g, 11.0 mmol), ammonium sulfate (2 mg), and hexamethyldisilazane (40 ml) was heated at reflux until a solution was attained (ca. 3 hrs). Excess hexamethyldisilazane was removed in vacuo and the trimethylsilyl derivative was used without further purification.

4. 5-Hydroxy-1-β-D-ribofuranosyl-1,2,3-triazole-4-carboxamide (1) and 5-Hydroxy-2-β-D-ribofuranosyl-1,2,3-triazole-4-carboxamide (2)

Method 1.

A solution of the trimethylsilyl derivative of 5-hydroxy-1,2,3-triazole-4-carboxamide (11.0 mmol), 1-0-acetyl-2,3,5-tri-0-benzoyl-β-D-ribofuranose (5.04 g, 10.0 mmol), and stannic chloride (0.84 ml, 7.2 mmol) in dry acetonitrile (100 ml) was stirred at room temperature for 20 hrs. The solvent was removed and chloroform (100 ml) was added to the syrup. Water (25 ml) was added to the mixture and the pH was adjusted to 7 with 5% aqueous sodium hydrogen carbonate. The organic layer was separated and dried over anhydrous magnesium sulfate. The drying agent was removed by filtration and the solvent was removed to give 5.50 g of syrup. The syrup was applied to a silica gel column (5 × 58 cm) packed in chloroform. Elution with chloroform-methanol (9:1) provided an amorphous mixture (3.50 g) of the two blocked nucleosides.

A mixture of the two blocked nucleosides (2.86 g, 5.0 mmol) in methanol (100 ml) saturated at 0° with ammonia was kept in a sealed pressure bottle at room temperature for 3 days. After removal of the solvent the residue was triturated with cold ethanol (15 ml). The insoluble material was removed by filtration, washed with cold ethanol, and dried to give 1.10 g of a mixture of the two deblocked nucleosides. A portion (1.00 g) of this mixture was applied to a cellulose (Avicel Micro Crystalline) column (4.5 × 42 cm) packed in n-butanol-acetic acid-water (5:2:3). The column was eluted with n-butanol-acetic acid-water (5:2:3, 1 liter); 20 ml fractions were collected. Fractions 28–32 provided 250 mg of the faster moving nucleoside. The compound was dissolved in hot water and decolorized with charcoal. The charcoal was removed by filtration thru Celite and the solution was concentrated in vacuo to 10 ml. The product was precipitated by addition of ethanol (ca. 25 ml). The compound was dried in vacuo at 80° C to give 150 mg of $\underline{3}$: m.p. >300°; $[\alpha]_D^{25}$ −63.4° (c 1.00, water); $\lambda_{max}^{pH1}$ 204 nm ($\epsilon$6750) and 257 nm ($\epsilon$9750), $\lambda_{max}^{pH7}$ 202 nm ($\epsilon$13,650) and 293 nm ($\epsilon$9050), $\lambda_{max}^{pH11}$ 227 nm ($\epsilon$850) and 293 nm ($\epsilon$8950).

Anal. Calcd for $C_8H_{12}N_4O_6 \cdot 2H_2O$: C, 32.43; H, 5.44; N, 18.91. Found: C, 32.26; H, 5.57; N, 18.71.

Fractions 34–46 provided 450 mg of the slower moving nucleoside. The compound was dissolved in hot water and decolorized with charcoal. The charcoal was removed by filtration thru Celite and the solution was concentrated in vacuo to 10 ml. The product was precipitated by addition of ethanol (ca. 25 ml). The compound was dried in vacuo at 80° to give 225 mg of $\underline{1}$: m.p. >300°; $[\alpha]_D^{25}$ −71.8° (c 1.00, water); $\alpha_{max}^{pH1}$ 222 nm ($\epsilon$7200) and 285 nm ($\epsilon$7650) $\lambda_{max}^{pH}$ 231 nm ($\epsilon$6200) and 270 nm ($\epsilon$11,000, $\lambda_{max}^{pH11}$ 233 nm ($\epsilon$5600) and 270 nm ($\epsilon$11,200).

Anal. Calcd for $C_8H_{12}N_4O_6 \cdot 2H_2O$: C, 32.43; H, 5.44; N, 18.91. Found: C, 32.56; H, 5.28; N, 18.91.

Method 2.

To a solution of ethyl malonamate (1.31 g, 10 mmol) in dry dimethylformamide (50 ml) was added sodium hydride (57% in oil) (420 mg, 10 mmol). The mixture was stirred until evolution of hydrogen ceased. To this solution was added 2,3,5-tri-O-benzoyl-β-$\underline{D}$-ribofuranosyl azide [J. Baddiley et al, *J. Chem. Soc.*, 4769 (1957)] (4.87 g, 10 mmol) and stirring at room temperature was continued for 18 hrs. After removal of the solvent the material was kept at room temperature for 3 days in a sealed pressure bottle with methanol (100 ml) saturated with ammonia at 0°. The methanolic ammonia was removed and the residue was triturated with ethanol (two 25-ml portions). The insoluble material was removed by filtration and dried to give 2.30 g of material. Column chromatography over cellulose (Avicel Micro Crystalline) using n-butanol-acetic acid-water (5:2:3) for elution provided 1.10 g of a mixture of $\underline{1}$ along with a small amount of a faster moving compound. Further chromatographic purification of this mixture over cellulose (Avicel Micro Crystalline) using mixtures of n-butanol-water and n-butanol-water-acetic acid provided a sample of $\underline{1}$ identical with the product obtained by Method 1.

5. Plaque Inhibition (Measles Virus)

Plaque inhibition experiments were conducted to study the effects of compounds prepared above against measles virus. Sixty mm culture plates containing VERO cells grown to confluency were infected with a known amount of measles virus. After 90 minutes of virus adsorption, 5 ml of an agar overlay was added in each dish and cells were incubated at 37°C in a humidified $CO_2$ incubator. The agar overlay consisted of Eagle's minimum essential medium +0.1% NaH $CO_3$ +2% fetal bovine serum +0.9% agar and various concentrations (0–500 μg/ml) of the compound. Following incubation at 37°C for 4 days, the cells were nourished with 2 ml of agar overlay containing 0.01% neutral red and the number of plague forming units (PFU) determined.

The data presented in Table I below indicate the extent of PFU inhibition at various concentrations of the compounds. An inhibition of 50% or more in PFU is considered to be a definite indication of the antiviral activity, from 20 to 50 as moderate antiviral activity whereas less than 20% inhibition is indicative of little or no antiviral activity. Concentrations of the compounds tested are on a weight rather than molar basis.

TABLE I

Plaque Inhibition (Measles Virus)

| Compound | Percent Plaque Inhibition at mg/ml | | |
|---|---|---|---|
| | 500 | 100 | 20 |
| 1 | 100 | 84 | 33 |
| 2 | 5 | 0 | 0 |
| 3 | 89 | 60 | 33 |
| 4 | 100 | 99 | 28 |

Compounds $\underline{1}$, $\underline{3}$ and $\underline{4}$ also proved active when tested in vitro against Type 1 herpes simplex according to the virus rating (VR) method of Sidwell, et al. Appl. Microbiol. 22, 797 (1971), exhibiting VR's of 0.6, 0.6 and 0.5, respectively.

We claim:

1. 5-Hydroxy-1-β-$\underline{D}$-ribofuranosyl-1,2,3-triazole-4-carboxamide.

2. The 5'-phosphate of the compound of claim 1.

* * * * *